United States Patent
Wilson

(10) Patent No.: US 10,588,728 B2
(45) Date of Patent: *Mar. 17, 2020

(54) INTRAORAL DEVICE HOLDER

(71) Applicant: NCASE INC, Las Vegas, NV (US)

(72) Inventor: Wesley P. Wilson, Las Vegas, NV (US)

(73) Assignee: NCASE INC, Las Vegas, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 15/964,799

(22) Filed: Apr. 27, 2018

(65) Prior Publication Data
US 2018/0243060 A1  Aug. 30, 2018

Related U.S. Application Data

(63) Continuation of application No. 15/444,009, filed on Feb. 27, 2017, now Pat. No. 9,980,799, which is a
(Continued)

(51) Int. Cl.
| | | |
|---|---|---|
| *G08B 21/00* | (2006.01) | |
| *A61C 19/02* | (2006.01) | |
| *A45D 44/20* | (2006.01) | |
| *A61C 7/08* | (2006.01) | |
| *A63B 71/08* | (2006.01) | |
| *B65D 43/16* | (2006.01) | |
| *G08B 21/18* | (2006.01) | |
| *H02J 7/02* | (2016.01) | |
| *A61C 7/00* | (2006.01) | |
| *A61C 13/00* | (2006.01) | |
| *A63B 71/00* | (2006.01) | |

(52) U.S. Cl.
CPC .............. *A61C 19/02* (2013.01); *A45D 44/20* (2013.01); *A61C 7/08* (2013.01); *A63B 71/085* (2013.01); *B65D 43/163* (2013.01); *G08B 21/18* (2013.01); *H02J 7/025* (2013.01); *A61C 7/00* (2013.01); *A61C 13/00* (2013.01); *A61C 2204/005* (2013.01); *A63B 71/0036* (2013.01)

(58) Field of Classification Search
CPC ..... A61C 19/02; A61C 7/08; A61C 2204/005; A61C 7/00; A61C 13/00; A63B 71/085; A63B 71/0036; H02J 7/025; A45D 44/20; G08B 21/18; B65D 43/163
USPC ................... 340/540, 539.21, 309.16, 568.1; 206/205; 368/10
See application file for complete search history.

(56) References Cited

U.S. PATENT DOCUMENTS

| | | |
|---|---|---|
| 4,615,681 A | 10/1986 | Schwarz |
| 5,020,037 A | 3/1991 | Raven |

(Continued)

*Primary Examiner* — Anh V La
(74) *Attorney, Agent, or Firm* — Charmasson, Buchaca Leach, LLP

(57) ABSTRACT

An intraoral device holder is provided. In some embodiments, the intraoral device holder may comprise a cavity and an occupancy configured to detect an intraoral device at least partially located within the cavity, and may further be configured to detect the absence of at least a portion of the intraoral device from the cavity. The intraoral device holder may further comprise a communication array that may be configured to transmit data corresponding to the intraoral device. In some embodiments, the occupancy sensor may be located at least partially above the floor.

20 Claims, 8 Drawing Sheets

Related U.S. Application Data continuation of application No. 14/882,558, filed on Oct. 14, 2015, now abandoned.

(60) Provisional application No. 62/063,647, filed on Oct. 14, 2014.

(56) References Cited

U.S. PATENT DOCUMENTS

| | | |
|---|---|---|
| 6,417,761 B1 | 7/2002 | Elliott |
| 9,980,799 B2* | 5/2018 | Wilson .................. A61C 19/02 |
| 2005/0285739 A1* | 12/2005 | Velhal ............... G08B 21/0227 340/572.1 |
| 2010/0102959 A1 | 4/2010 | Ashrafzadeh et al. |
| 2010/0164716 A1 | 7/2010 | Estevez et al. |
| 2014/0134561 A1* | 5/2014 | Smith .................... G16H 40/63 433/6 |
| 2015/0320643 A1 | 11/2015 | Zhou |

* cited by examiner

INTRAORAL DEVICE HOLDER

CROSS-REFERENCE TO RELATED APPLICATIONS

This application is a continuation of U.S. patent application Ser. No. 15/444,009, filed on 2017 Feb. 27, which is a continuation of U.S. patent application Ser. No. 14/882,558, filed 2015 Oct. 14, which claims the benefit of U.S. Provisional Utility Patent Application No. 62/063,647, filed 2014 Oct. 14, all of which are herein incorporated by reference.

FIELD OF THE INVENTION

This patent specification relates to the field of intraoral device holders. More specifically, this patent specification relates to intraoral device holders configured to provide information corresponding to an intraoral device.

BACKGROUND

Intraoral devices are used for a variety of purposes and may include dental appliances, sleep apnea machines, retainers, dentures, partial dentures, active aligners, protraction headgear, spring aligners, and the like. Users of these devices and appliances face similar problems regardless of the type of devices and appliance. For instance, intraoral device users often face a problem of remembering to wear their appliance. By forgetting to wear a retainer, the user may encounter treatment setbacks such as their teeth shifting or not moving correctly requiring a lengthy and uncomfortable treatment period.

Users may also encounter the problem of remembering where they left their intraoral device. These appliances are usually expensive and difficult to replace. Much time and energy can be wasted on looking for lost appliances. If the appliance cannot be found, in addition to possible treatment setbacks, a user may be required to pay for a replacement appliance.

For intraoral devices such as retainers, a user may have trouble remembering the amount of time they have been wearing their intraoral device each day. Without an accurate accounting of the amount of time the retainer has been worn, a user may also encounter treatment setbacks such as their teeth shifting or not moving correctly requiring a lengthy and uncomfortable treatment period.

Therefore, a need exists for novel apparatuses for reminding a user to wear their intraoral device. There also exists a need for novel apparatuses for preventing the loss of intraoral devices. There is a further need for novel apparatuses for facilitating locating intraoral devices. Finally, there exists a need for novel apparatuses for recording and reporting the amount of time an intraoral device is worn by a user.

SUMMARY

In some embodiments, an intraoral device holder may comprise a cavity structured to at least partially receive an intraoral device. The intraoral device holder may also comprise an occupancy sensor that may be configured to detect the presence of the intraoral device that is at least partially located within the cavity, and may also be configured to detect the absence of at least a portion of the intraoral device from the cavity.

In some embodiments, an intraoral device holder may comprise a cavity that is configured and/or structured to at least partially receive an intraoral device. The intraoral device holder may further comprise an occupancy sensor that may be configured to detect whether the intraoral device is at least partially located within the cavity. Still further, the intraoral device holder may comprise a communication array that may be configured to transmit data corresponding to one or more feature of the intraoral device, wherein the one or more feature has been detected while the intraoral device was located within the cavity.

In some embodiments, an intraoral device storage device comprises a cavity that may be structured to at least partially receive an intraoral device, wherein the cavity may comprise a floor. The intraoral device storage device may also comprise an occupancy sensor that is at least partially located above the floor. The cavity may be further structured so that at least a portion of the intraoral device may directly contact the floor, when the intraoral device is at least partially positioned within the cavity.

BRIEF DESCRIPTION OF THE DRAWINGS

Some embodiments of the present invention are illustrated as an example and are not limited by the figures of the accompanying drawings, in which like references may indicate similar elements and in which.

DESCRIPTION OF THE EXEMPLARY EMBODIMENTS

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
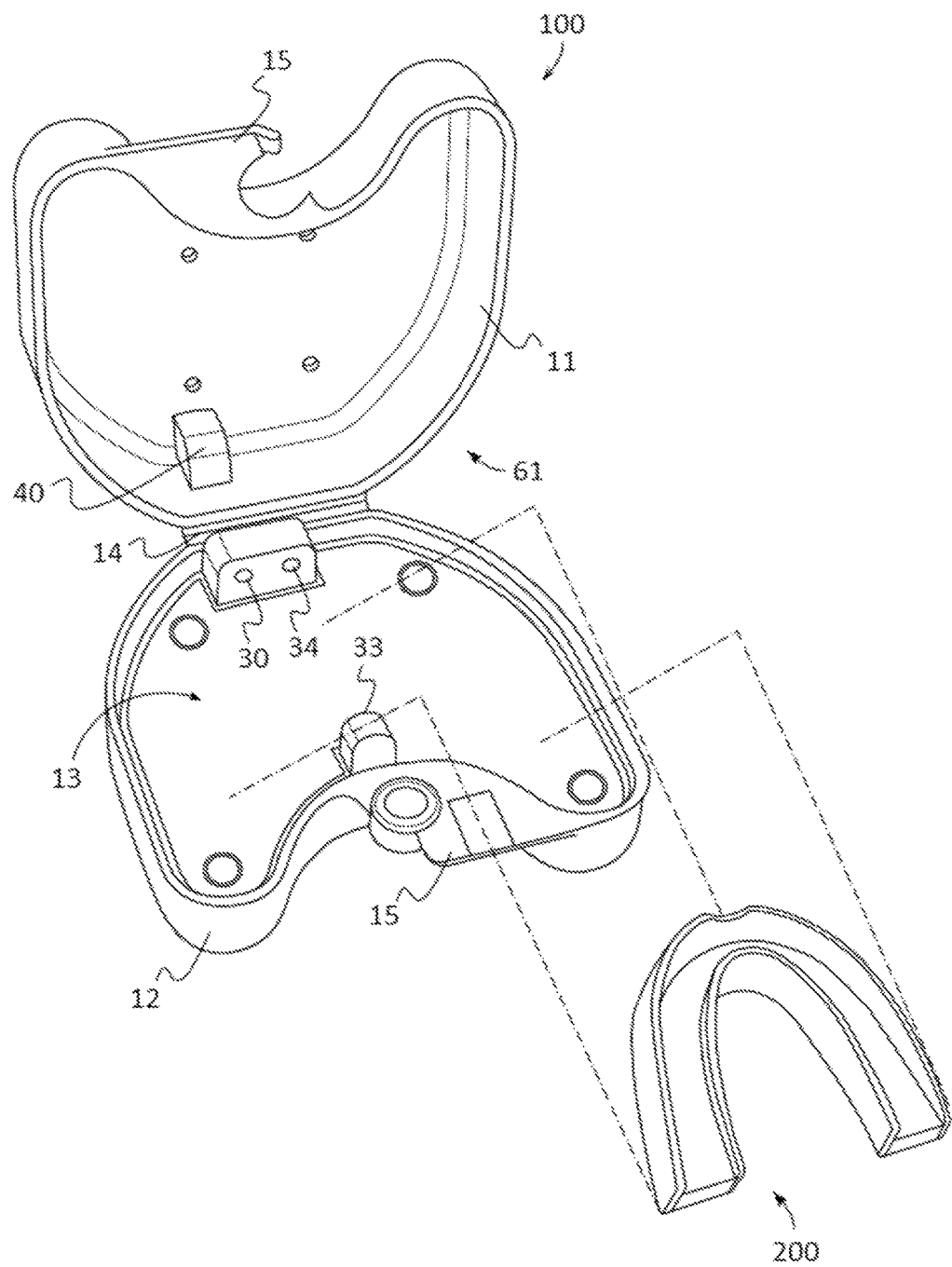
FIG. 1 depicts a top perspective view of an example of an intraoral device holder in an open position showing insertion of an intraoral device into the intraoral device holder according to various embodiments described herein.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

New intraoral storage devices are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

Figure 2:
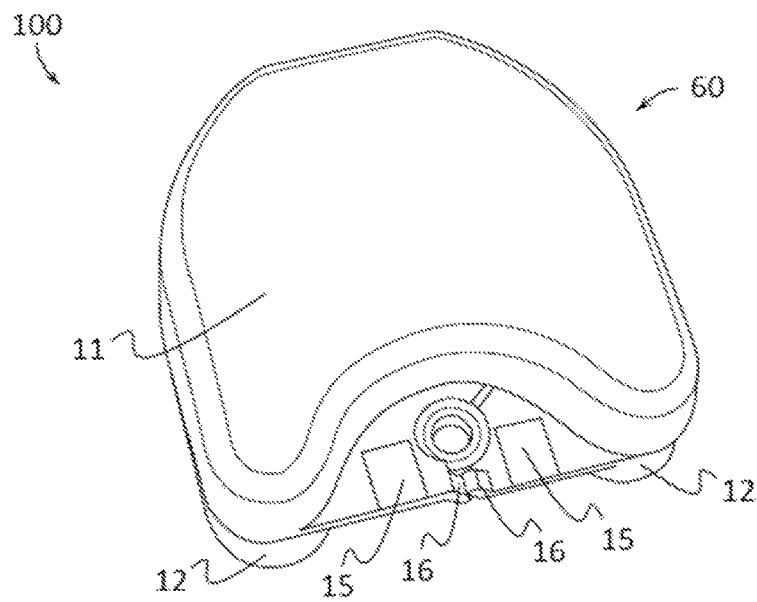
FIG. 2 illustrates a top perspective view of an example of an intraoral device holder in a closed position according to various embodiments described herein.
Figure 3:
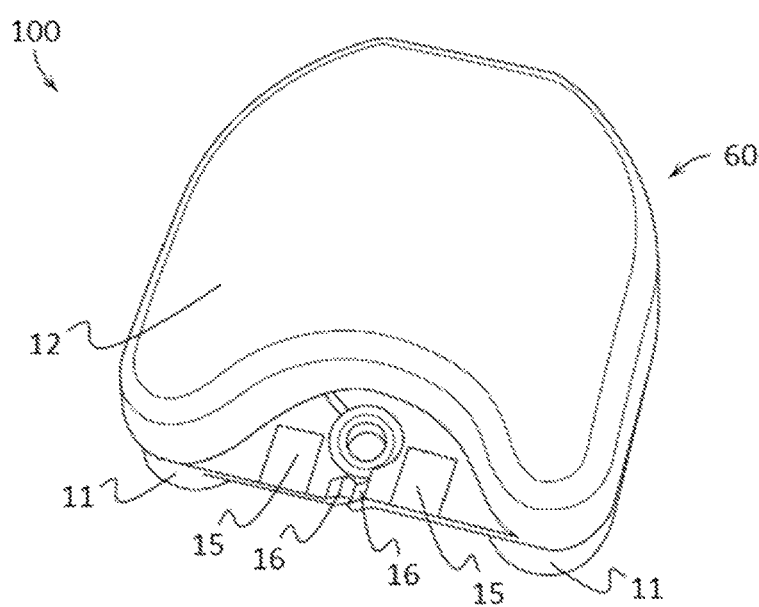
FIG. 3 shows a bottom perspective view of an example of an intraoral device holder in a closed position according to various embodiments described herein.

The present invention will now be described by example and through referencing the appended figures representing preferred and alternative embodiments. FIGS. 1-3 depict an example of an intraoral device holder ("the case") 100 according to various embodiments. In some embodiments, the case 100 may comprise a lid 11 and a base 12 which may be temporarily aligned and brought together as shown in FIGS. 2 and 3, to form a cavity 13 between the lid 11 and base 12 that is configured to receive a power source 36 (FIGS. 5-8), an occupancy sensor 32 (FIG. 8), a processing unit 21 (FIGS. 8 and 9), one or more alert devices 35, 38, 39 (FIGS. 7 and 8) and any other component of the case 100. In further embodiments, the case 100 may comprise a lid 11 and a base 12 which may be temporarily aligned and brought together as shown in FIGS. 2 and 3, to form a cavity 13 between the lid 11 and base 12 that is configured to receive a power source 36, an alert device 35, 38, 39, an occupancy sensor 32, a processing unit 21, any other component of the case 100, and an intraoral device 200 (FIG. 1). The cavity 13 may be configured to define a volume which is suitable for receiving an intraoral device 200 such as a retainer, mouth guard, or the like. In further embodiments, the case 100 may comprise an optional hinge 14 and an optional lid release 15 both providing an engagement with a base 12. A hinge 14 may pivotally couple a portion of the lid 11 to the base 12 while the lid release 15 may removably couple another portion of the lid 11 to the base 12. In still further embodiments, a lid 11 may comprise a lid release 15 and a base 12 may also comprise a lid release 15. When the lid 11 and base 12 are pivoted into a closed position 60 (FIGS. 2 and 3), a first lid release 15 may be removably coupled to a second lid release 15 and/or to a portion of the lid 11 and/or base 12 thereby closing off the cavity 13 and maintaining the case in a closed position 60. By uncoupling a first lid release 15 from a second lid release 15 and/or a portion of the lid 11 and/or base 12, portions of the lid 11 may be moved away from the base 12, such as by pivoting, thereby moving the case 100 into an open position 61 and granting access for insertion and removal of an intraoral device 200 to and from the cavity 13.

In some embodiments, a lid 11 and a base 12 may comprise a generally rectangular prism shape with rounded corners, and when aligned and brought together, form a cavity 13 (FIG. 3) or space between the two that is able to receive a retainer, denture, and other like intraoral devices 200. In other embodiments, a cavity 13, lid 11 and/or a base 12 may be configured in a plurality of sizes and shapes including circular shaped, oval shaped, triangular shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes may be made without departing from the spirit or scope of the invention.

In some embodiments, one or more hinges 14 may be positioned anywhere on the case 100 to provide a pivotal joining engagement between the lid 11 and the base 12. A hinge 14 may comprise a butt hinge, butterfly hinge, flush hinge, barrel hinge, concealed hinge, continuous hinge, T-hinge, strap hinge, double-acting hinge, Soss hinge, a flexible material hinge, or any other type or style of hinge or pivotal joining method that allows portions of a lid 11 and base 12 to be pivoted away from each other. In further embodiments, a hinge 14 may comprise any type of hinge known in the art, including so-called "living" hinges, which typically comprise a linear, relatively flexible area between two relatively more rigid components, such as a line of thin plastic between thicker plastic portions, as is well known in the art. In some embodiments, a hinge 14 may comprise a spring or other tension providing device that is able to mechanically assist with the opening or closing of the lid 11. In other embodiments, a lid 11 and base 12 may be slidably joined together with a tongue and groove engagement allowing portions of a lid 11 to be slid open and closed from the base 12. In further embodiments, a lid 11 and base 12 may be joined with any other type of engagement that allows a portion of a lid 11 to be moved towards and away from a base 12 thereby restricting and granting access to the cavity 13 of the case 100.

In some embodiments, one or more lid releases 15 may be positioned anywhere on the case 100 that are configured to temporarily allow or deny a portion of a lid 11 from moving with respect to the base 12 by temporarily engaging a portion of the lid 11 to the base 12. In further embodiments, a lid release 15 may comprise a pressure catch 16 that may be configured to secure or engage a portion of the lid 11 to the base 12 when a portion of the lid 11 is pressed against the base 12 and/or lid release 15 such as when the case 100 is in a closed position 60 (FIGS. 2 and 3). By pressing on the lid release 15, when the case 100 is in a closed position 60, the pressure catch 16 may be released allowing portions of the lid 11 to move away from the base 12 allowing the base to be in an open position 61 as shown in FIG. 1. In other embodiments, a lid release 15 may be configured to temporarily join or engage a portion of a lid 11 to a base 12 with a clasp type connection method, magnetic lock type connection method, key lock type connection method, electronic lock type connection method, combination lock type connection method, push-to-lock type connection method, a turn-to-lock type connection method, slide-to-lock type connection method or any other suitable temporary connection method as one reasonably skilled in the art could envision to serve the same function.

As shown in the example of FIG. 1, the case 100 is illustrated in an open position 61 with a portion of the lid 11 pivoted away from the base 12 while still being engaged together at a hinge 14. The cavity 13 formed between the base 12 and lid 11 is configured to receive and secure a retainer, denture, or other like intraoral device 200. In some embodiments, the case 100 may comprise a floor 18 which may be configured to separate electronic components of the case 100 from an intraoral device 200 received in the cavity 13. In some embodiments, a floor 18 may be joined to or coupled to the base 12 with electronic components stored between the floor 18 and the base 12. In other embodiments, a floor 18 may be joined to or coupled to the lid 11 with electronic components stored between the lid 11 and the floor 18. In further embodiments, a floor 18 may be joined or coupled to the base 12 and/or lid 11 with electronic components stored between the lid 11 and the floor 18 and/or the base 12 and the floor 18. A floor 18 may be joined or coupled to a lid 11 or base 12 to prevent fluids and debris associated with an intraoral device 200 received in the cavity 13 from reaching the electronic components of the case 100.

Figure 4:
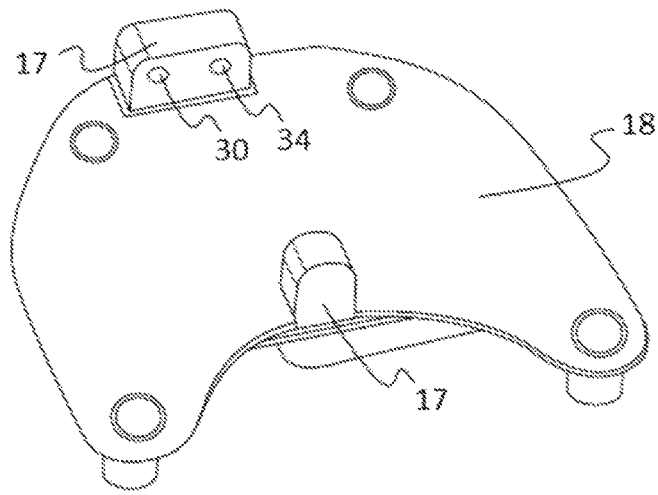
FIG. 4 depicts a top perspective view of an example of a floor according to various embodiments described herein.

FIG. 4 depicts a top perspective view of an example of a floor 18 according to various embodiments described herein. In some embodiments, a floor 18 may comprise or be coupled to one or more electronic components such as a lid sensor 30, a control input 31, and/or an occupancy sensor 32 (FIG. 8) which may include a sensor receiver 34, and/or a sensor emitter 33. In preferred embodiments, electronic components of the floor 18 and/or coupled to the floor 18 may be water proof and may be in electrical communication with other electronic components located or stored between the lid 11 and the floor 18 and/or the base 12 and the floor 18. Optionally, one or more sensor housings 17 may be coupled to the floor 18 to provide structures for one or more sensors and other electronic components to be positioned on or within. In some embodiments, a sensor emitter 33 may be coupled in a first sensor housing 17 and a sensor receiver 34 may be coupled within a second sensor housing 17. The sensors 33, 34, may use infrared light to detect if an intraoral device 200 (FIG. 1) is within the cavity 13 (FIG. 1) such as by detecting if the intraoral device interrupts the infrared light. By disposing the sensors 33, 34, within the sensor housings 17, the sensor housings 17 may act as infrared light and sensor shields.

In some embodiments, a case 100 may comprise an occupancy sensor 32 (FIG. 8) which may include a sensor receiver 34 and/or a sensor emitter 33 which are configured to detect an intraoral device 200 (FIG. 1). The sensor receiver 34 may comprise an infrared light receiver or detector and a sensor emitter 33 may comprise an infrared light emitter. In further embodiments, an intraoral device 200 placed proximate to a sensor receiver 34 and/or a sensor emitter 33, such as in the cavity 13, may be detected as it interrupts the path of infrared light between an infrared sensor emitter 33 and an infrared sensor receiver 34. When the infrared light is not interrupted, the infrared sensor receiver 34 and infrared sensor emitter 33 may be used to detect that an intraoral device 200 is not proximate to a sensor receiver 34 and/or a sensor emitter 33, such as not in the cavity 13.

Figure 5:
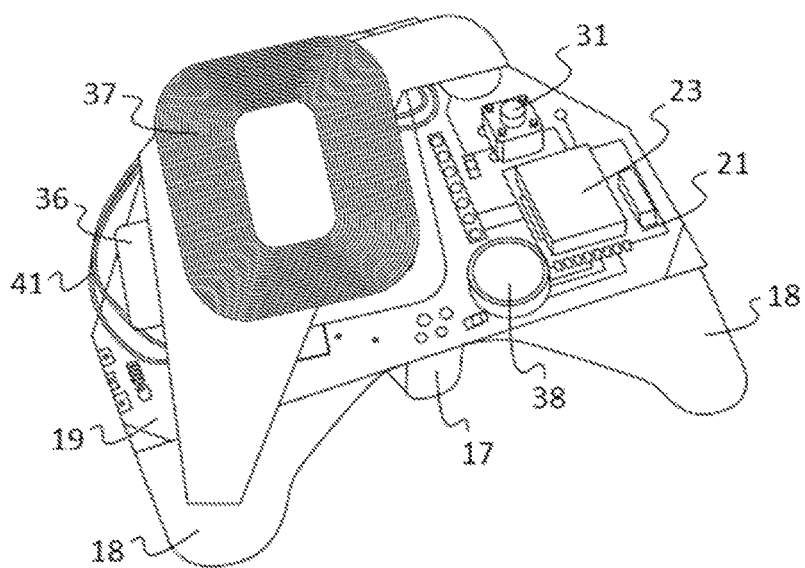
FIG. 5 illustrates a bottom perspective view of an example of a floor assembled with some components of an intraoral device holder according to various embodiments described herein.
Figure 6:
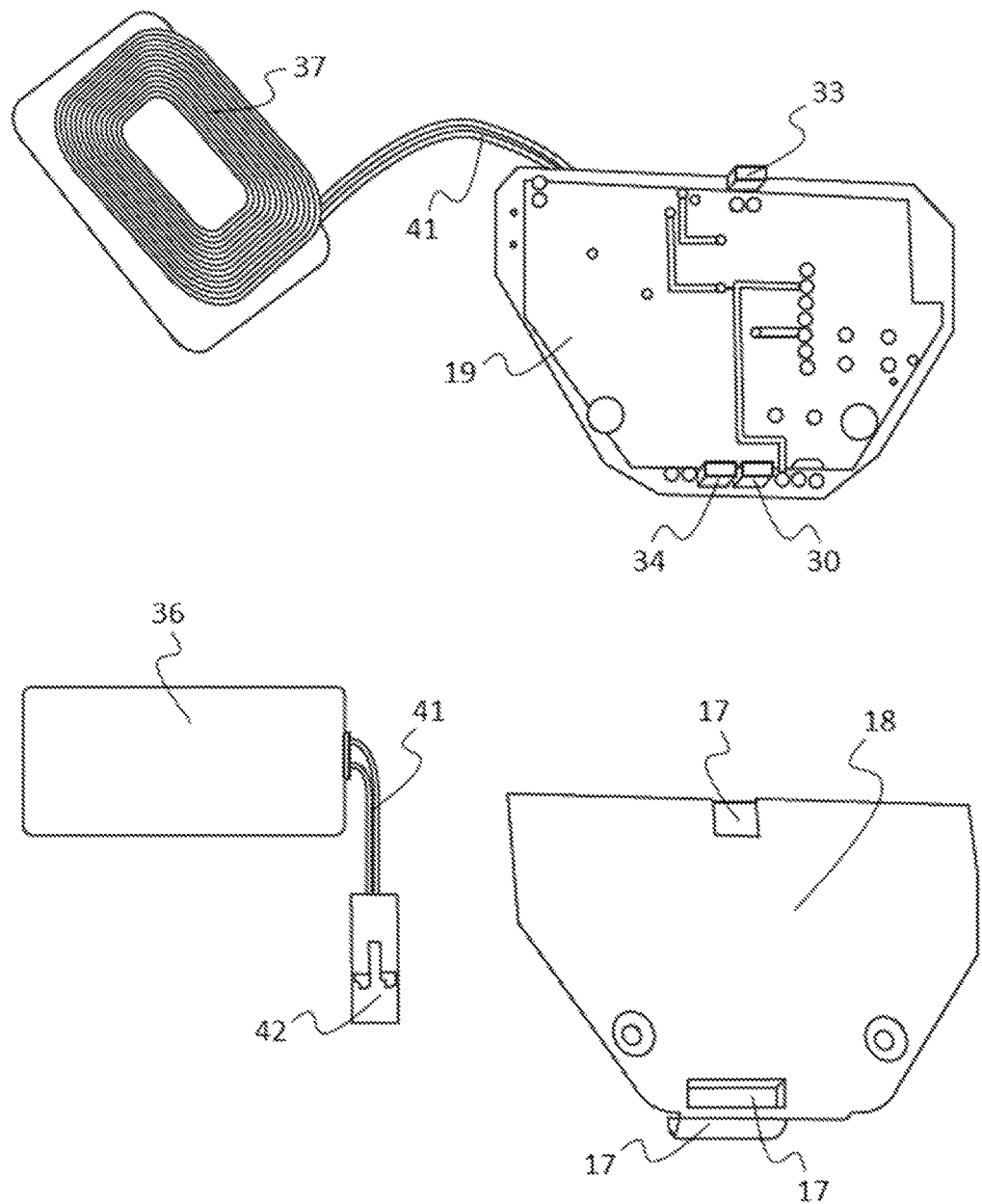
FIG. 6 shows a perspective exploded top view some of the components of an intraoral device holder according to various embodiments described herein.
Figure 7:
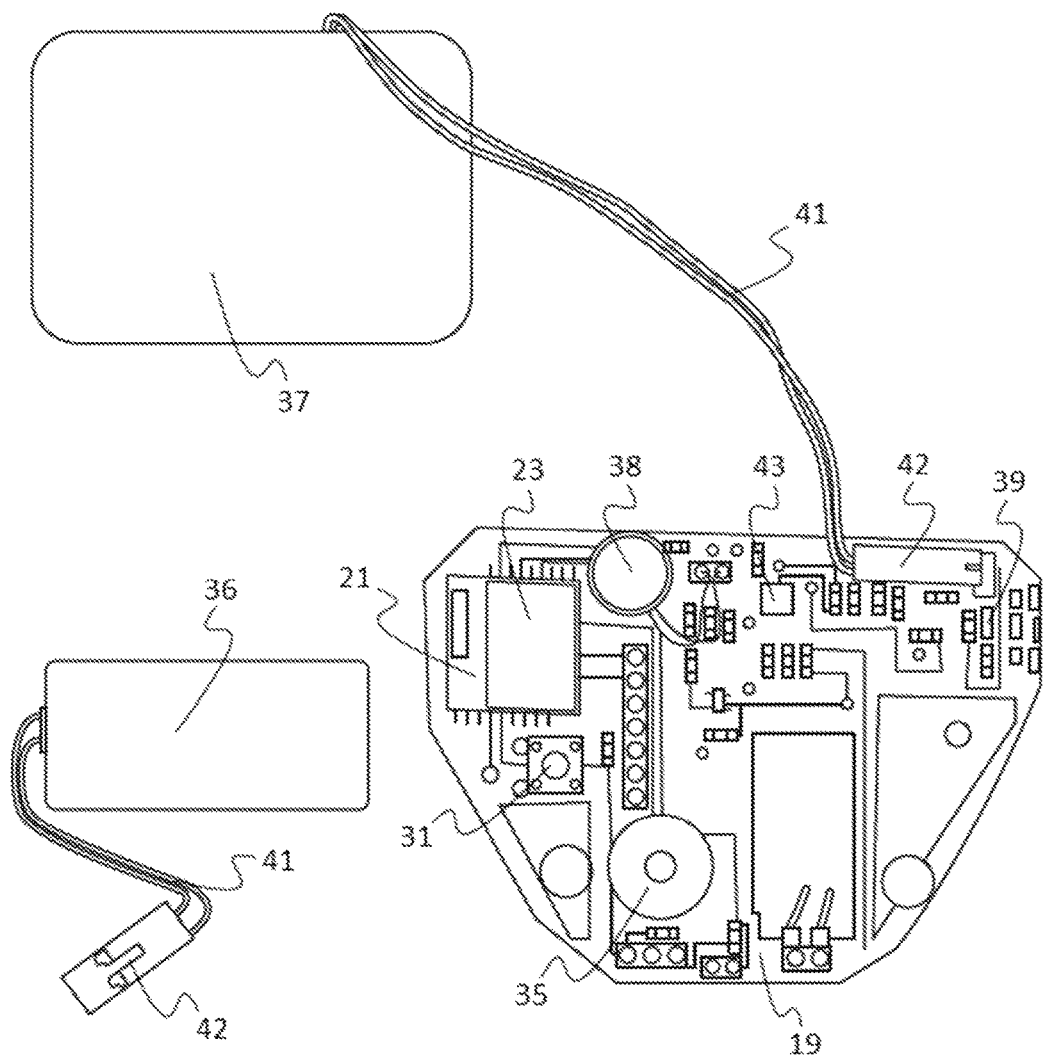
FIG. 7 depicts a perspective exploded bottom view some of the components of an intraoral device holder according to various embodiments described herein.
Figure 8:
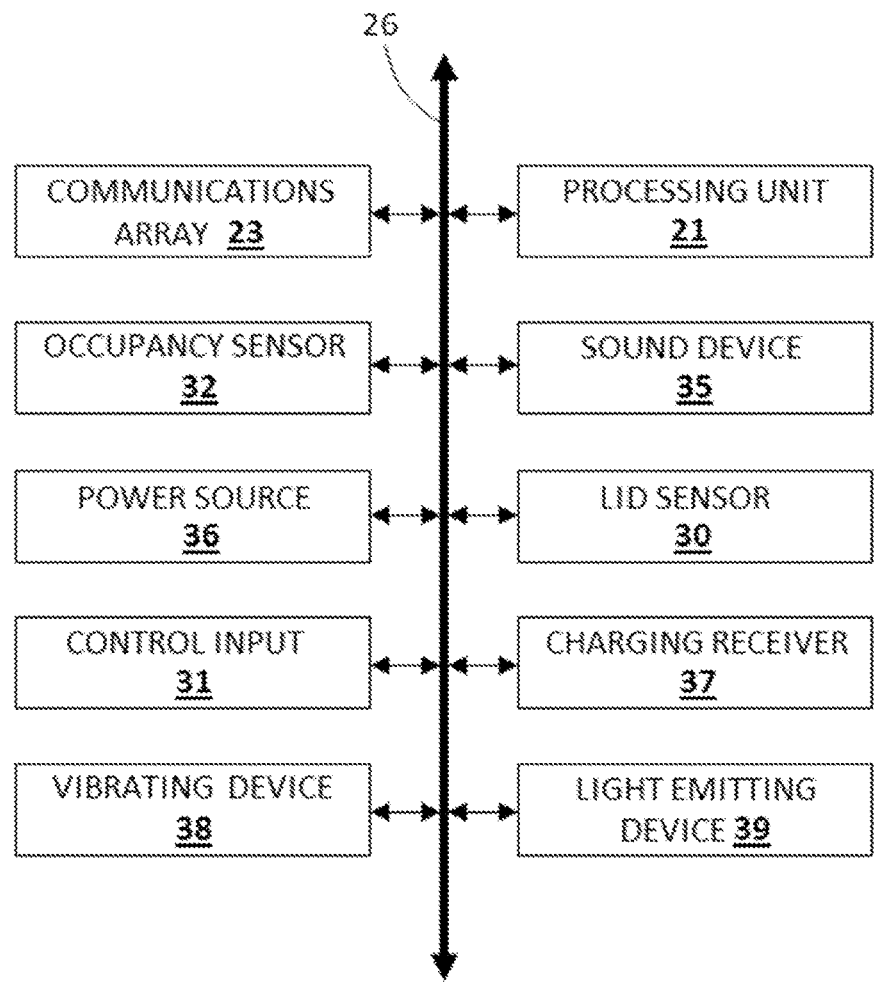
FIG. 8 illustrates a block diagram of some of the components of an intraoral device holder according to various embodiments described herein.

FIGS. 5-7 illustrate examples of some electronic components of an intraoral device holder 100 (hereinafter "case") and some optional configurations that they may be assembled in, while FIG. 8 illustrates a block diagram of some of the electronic components of a case 100 according to various embodiments described herein. In some embodiments, a case 100 may comprise a circuit board 19 which may be positioned between a base 12 and a floor 18. In other embodiments, a circuit board 19 may be positioned between a lid 11 and a floor 18. A circuit board 19 may comprise and/or provide electrical communication between one or more electronic components such as a processing unit 21, a lid sensor 30, a control input 31, a sensor receiver 34, a sensor emitter 33, an alert device 35, 38, 39 and/or a communications array 23. In further embodiments, a circuit board 19 may comprise a local bus 26 which may provide electrical communication between one or more electronic components.

In some embodiments, a circuit board 19 may comprise a printed circuit board (PCB) which mechanically supports and electrically connects electronic components using conductive tracks, pads and other features etched from copper sheets laminated onto a nonconductive substrate. PCBs can be single sided (one copper layer), double sided (two copper layers) or multi-layer. Conductors on different layers may be connected with plated-through holes called vias. In some embodiments, a circuit board 19 may only comprise copper connections and no embedded components and may be called a printed wiring board (PWB) or etched wiring board. In other embodiments, a circuit board 19 may comprise a printed circuit assembly (PCA), printed circuit board assembly or PCB assembly (PCBA), a circuit card assembly (CCA), or a backplane assembly, or any other suitable electrical connection and communication method including standard wiring and the like.

In some embodiments, a case 100 may comprise a lid sensor 30 such as a magnetic sensor that is operable to detect if the lid 11 is open, closed, and/or optionally partially opened or closed. In further embodiments, a lid sensor 30 may comprise a Hall effect sensor which may be positioned on the floor 18, base 12, and/or lid 11 and which may detect increases or decreases, and therefore proximity, in an electric field generated by the magnetic material of a magnet 40 (FIG. 1) which may be complementarily positioned on the floor 18, base 12, and/or lid 11 to detect if the lid 11 is open, closed, and/or partially opened or closed. In other embodiments, a lid sensor 30 may comprise a pressure switch, an electrical circuit, or any other method configured to detect if the lid is open, closed, or optionally not open or closed. In further embodiments, a case 100 may comprise a reed switch, a pressure sensor, a contact sensor, a button mount, an ambient light sensor, or any other suitable sensor to detect if the lid 11 is open, closed, or partially opened or closed.

In some embodiments, a case 100 may comprise a control input 31 which may be configured to control a function of an electronic component. In further embodiments, a control input 31 may comprise an input such as turnable control knobs, depressable button type switches, slide type switches, rocker type switches, or any other suitable input that may be used to modulate electricity between one or more electronic components of the case 100 to control a function of the case 100.

In some embodiments, a case 100 may comprise an occupancy sensor 32 which may include a sensor receiver 34 and/or a sensor emitter 33 which are configured to detect if an intraoral device 200 (FIG. 1) is in the cavity 13. In further embodiments, an occupancy sensor 32 may comprise an RFID sensor receiver, a magnetic sensor receiver, an Ultraviolet light receiver, an optical receiver, or any other sensor receiver that may be used to detect the presence or absence of an intraoral device 200 in a cavity 13. In still further embodiments, an occupancy sensor 32 may comprise a RFID emitter, a magnetic field generating material such as magnetic metals and permanent magnets, an Ultraviolet light emitter, an optical light emitter or any other sensor receiver that may be used to detect the presence or absence of an intraoral device 200 in a cavity 13. In even further embodiments, a case 100 may comprise a reed switch, a button mount, a force sensor, an ambient light sensor, or any other suitable sensor to detect the presence or absence of an intraoral device 200 in a cavity 13.

In some embodiments, a case 100 may comprise a power source 36, such as a rechargeable and/or replaceable battery, which may provide electrical power to the electronic components of the case 100. A power source 36 may be positioned anywhere in the case 100 such as between the floor 18 and the base 12 (FIGS. 1-3). One or more wires 41, electrical clips 42, or other electrical couplings may provide electrical communication between the power source 36 a circuit board 19 or local bus 26. In further embodiments, a case 100 may comprise a charging receiver 37 which may be in electrical communication with a power source 36 such as a rechargeable battery. One or more wires 41, electrical clips 42, or other electrical couplings may also provide electrical communication between a charging receiver 37 and the power source 36, circuit board 19, and/or local bus 26. In still further embodiments, a charging receiver 37 may comprise a wireless charging receiver, such as a Qi Standard Wireless charging Receiver or any other inductive charging or wireless power receiver, which may be configured to receive energy through an inductive coupling and to electrically communicate the energy to the power source 36 or a power management microchip 43 in electronic communication with the charging receiver 37 allowing wireless energy to inductively charge the power source 36. In still further embodiments, a charging receiver 37 may comprise an electrical connector such as a USB connector such as a micro-USB, mini-USB, Type A USB plug, Type B USB plug, Mini-A USB plug, Mini-B USB plug, Micro-A USB plug, Micro-B USB plug, Micro-B USB 3.0 plug, ExtMicro USB plug, Lightning plug, 30-pin dock connector, Pop-Port connector, Thunderbolt plug, Firewire plug, Portable Digital Media Interface (PDMI) plug, coaxial power connector plug, barrel connector plug, concentric barrel connector plug, tip connector plug, or any other plug, connector, or receptacle capable of electrical communication.

In some embodiments, a case 100 may comprise one or more alert devices such as one or more sound devices 35 which may comprise a speaker which may be operable to produce or create one or more audible alert sounds at one or more volume levels. In further embodiments, a sound device 35 may comprise a buzzer, a piezoelectric sound producing device, a dielectric elastomer sound producing device, a buzzer, a moving coil loudspeaker, an electrostatic loudspeaker, an isodynamic loudspeaker, a piezo-electric loudspeaker, or any other device capable of producing one or more sounds. In further embodiments, a case 100 may comprise one or more alert devices such as one or more vibration devices 38, light emitting devices 39, and/or a sound devices 35 configured to relay haptic, visual, and/or auditory alert information from a case 100 to a user. A light emitting device 39 may include a light emitting diode (LED), incandescent light bulb, halogen light bulb, laser light emitter, electroluminescent light source, neon light source, or any other suitable light source which is able to emit light, such as constant on light or intermittent light in one or more colors and/or intensities, viewable by a user as an alert.

In some embodiments, a case 100 may comprise one or more alert devices such as one or more vibrating devices 38 configured to produce vibrations. In further embodiments, a vibrating device 38 may comprise a long life brushless (BLDC) vibration motor, a coin or pancake vibration motor, an encapsulated vibration motor, an enclosed vibration motor, a pager motor, an eccentric rotating mass (ERM) motor, a linear resonant actuator (LRA), a printed circuit board (PCB) mounted vibration motor, or any other electrical device capable of producing vibrations.

In some embodiments, a case 100 may comprise a communications array 23 which is operable to send and receive wireless and/or wired communications. In further embodiments, a communications array 23 may comprise a Bluetooth receiver and transmitter and which enables wireless communication to a network or an external access client device (FIG. 10) such as cell phones, smart phones 300A, tablet computers, laptop computers 300B, wearable computers such as watches, Google Glasses, etc. and the like. In other embodiments, a communications array 23 may comprise a receiver and transmitter which enables any number of suitable wireless data communication protocols, techniques, or methodologies including, without limitation: RF; IrDA (infrared); Bluetooth; Wifi; ZigBee (and other variants of the IEEE 802.15 protocol); IEEE 802.11 (any variation); IEEE 802.16 (WiMAX or any other variation); Direct Sequence Spread Spectrum; Near-Field Communication (NFC); Frequency Hopping Spread Spectrum; Long Term Evolution (LTE); cellular/wireless/cordless telecommunication protocols (e.g. 3G/4G, etc.); iBeacon; wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication.

Figure 9:
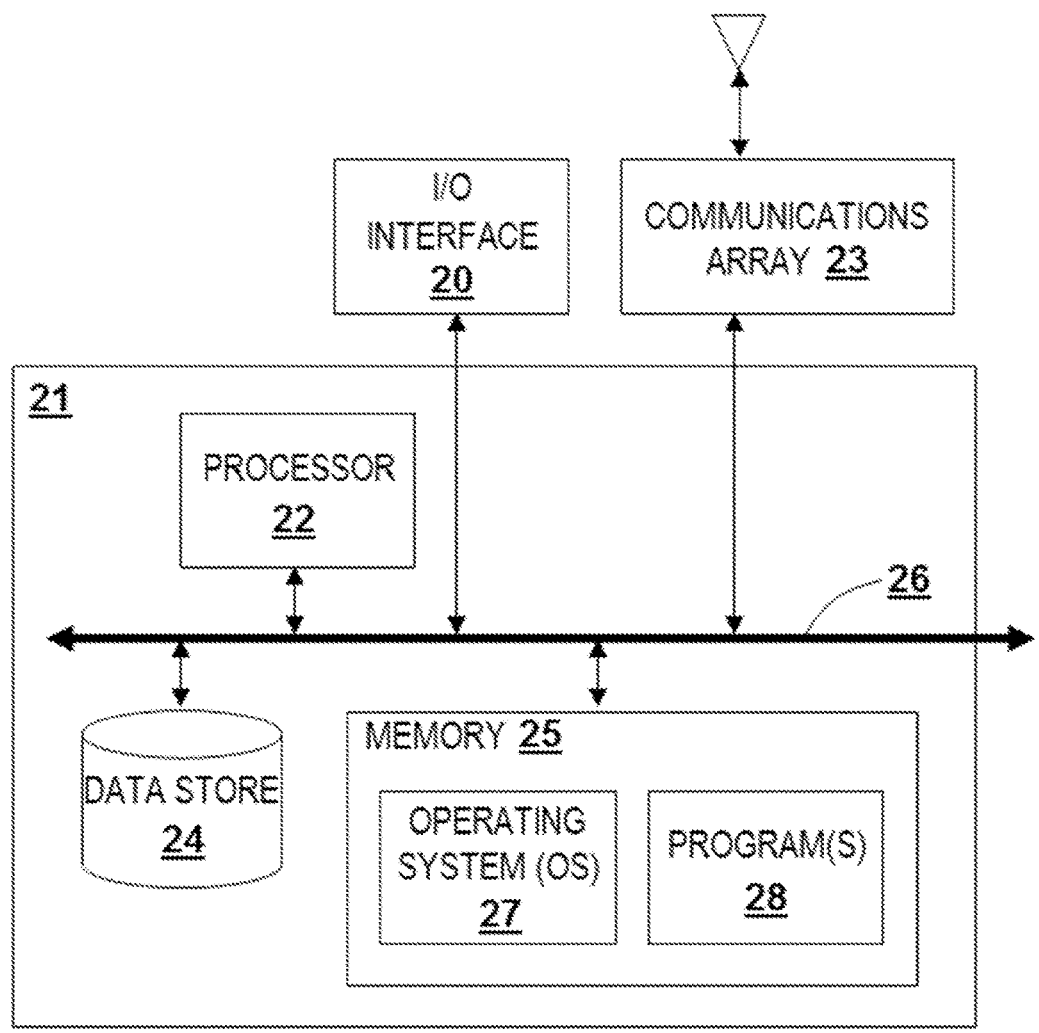
FIG. 9 shows a block diagram of some of the components of a processing unit according to various embodiments described herein.

FIG. 9 shows a block diagram of some of the components of a processing unit 21 according to various embodiments described herein. In some embodiments, a processing unit 21 may comprise a small computer on a single integrated circuit typically used for embedded applications and preferably comprising a processor core, memory, and programmable input/output peripherals. Program memory in the form of NOR flash or OTP ROM may also be included on chip, as well as a typically small amount of RAM. A processing unit 21 may be used to receive input from, control, or modulate one or more of the functions of any electronic component of the case 100.

The processing unit 21 may be configured to trigger one or more alerts or notifications which may be produced by a component of the case 100 in response to an electronic communication from a communications array 23, an occupancy sensor 32, a lid sensor 30, a power source 36, and/or a control input 31. An alert may include audible, tactile, and visual alerts. In some embodiments, a processing unit 21 may be configured to produce an audible alert by operating a sound device 35 to produce or create one or more audible sounds at one or more volume levels. In some embodiments, a processing unit 21 may be configured to produce a tactile alert by operating a sound device 35 to produce or create one or more vibrations which may vibrate the case 100 to produce a tactile alert perceptible by touch. In some embodiments, a processing unit 21 may be configured to produce a visual alert by operating a light emitting device 39 or any other type of light emitting element to produce or create one or more colors of light at one or more brightness intensities which may illuminate to produce a visual alert.

In further embodiments, a processing unit 21 may be a digital device that, in terms of hardware architecture, generally includes a processor 22, a data store 24, and memory 25. The processing unit 21 may be in electrical communication with a communications array 23 and one or more input/output (I/O) interfaces 20, such as a lid sensor 30, control input 31, occupancy sensor 32, sensor receiver 34, sensor emitter 33, sound device 35, power source 36, charging receiver 37, a vibration device 38, and/or a light emitting device 39. It should be appreciated by those of ordinary skill in the art that FIG. 9 depicts the processing unit 21 in an oversimplified manner, and a practical embodiment may include additional components and suitably configured processing logic to support known or conventional operating features that are not described in detail herein.

The components (22, 23, 24, 25, 27, 28, and 30) are communicatively coupled via a local interface 26. The local interface 26 can be, for example but not limited to, one or more buses or other wired or wireless connections, as is known in the art. The local interface 26 can have additional elements, which are omitted for simplicity, such as controllers, buffers (caches), drivers, repeaters, and receivers, among many others, to enable communications. Further, the local interface 26 may include address, control, and/or data connections to enable appropriate communications among the aforementioned components.

The processor 22 is a hardware device for executing software instructions. The processor 22 can be any custom made or commercially available processor, a central processing unit (CPU), an auxiliary processor among several processors associated with the processing unit 21, a semiconductor-based microprocessor (in the form of a microchip or chip set), or generally any device for executing software instructions. When the processing unit 21 is in operation, the processor 22 is configured to execute software stored within the memory 25, to communicate data to and from the memory 25, and to generally control operations of the processing unit 21 pursuant to the software instructions. In an exemplary embodiment, the processor 22 may include a mobile optimized processor such as optimized for power consumption and mobile applications.

The I/O interfaces 20 may include any other electronic component of the case 100, such as a lid sensor 30, control input 31, occupancy sensor 32, sensor receiver 34, sensor emitter 33, sound device 35, power source 36, charging receiver 37, a vibration device 38, and/or a light emitting device 39 may be used to receive input from and/or for providing output from the case 100. Input can be provided via, for example, a lid sensor 30, control input 31, occupancy sensor 32, sensor receiver 34, sensor emitter 33, and/or charging receiver 37. System output can be provided via a communications array 23, a light emitting device 39, a vibration device 38, and/or a sound device 35. The I/O interfaces 20 can also include, for example, a charging indicator light emitting device 39 or any other type of light emitting device which may be positioned anywhere on the case 100, a serial port, a parallel port, a small computer system interface (SCSI), an infrared (IR) interface, a radio frequency (RF) interface, a universal serial bus (USB) interface, and the like. The I/O interfaces 20 can include a graphical user interface (GUI) that enables a user to interact with the processing unit 21. Additionally, the I/O interfaces 20 may further include an imaging device, i.e. camera, video camera, etc.

The memory 25 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 25 may incorporate electronic, magnetic, optical, and/or other types of storage media. Note that the memory 25 may have a distributed architecture, where various components are situated remotely from one another, but can be accessed by the processor 22. The software in memory 25 can include one or more software programs, each of which includes an ordered listing of executable instructions for implementing logical functions. In the example of FIG. 9, the software in the memory 25 includes a suitable operating system (O/S) 27 and programs 28. The operating system 27 essentially controls the execution of other computer programs, and provides scheduling, input-output control, file and data management, memory management, and communication control and related services. The programs 28 may include various applications, add-ons, etc. configured to provide end user functionality with the processing unit 21. For example, exemplary programs 28 may include, but not limited to, a clock or timer program which may be configured to track input form an I/O interface 20 and to correlate the input with a time stamp or time period. In a typical example, the end user typically uses one or more of the programs 28 to control the functions of the electronic components of the case 100.

Figure 10:
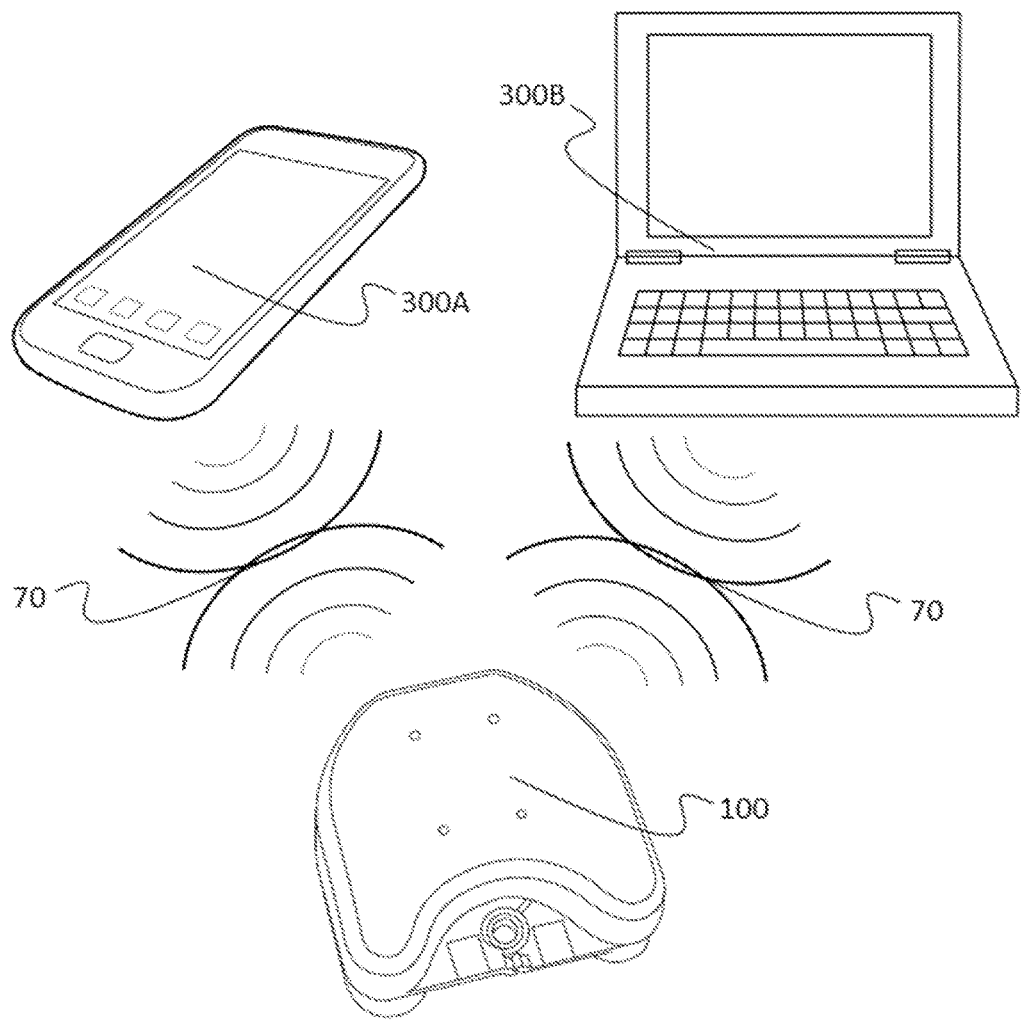
FIG. 10 depicts a perspective view of an example of an intraoral device holder in wireless communication with client devices according to various embodiments described herein.

FIG. 10 depicts a perspective view of an example of an intraoral device holder 100 in wireless communication 70 with client devices according to various embodiments described herein. In some embodiments, a processing unit 21 and communications array 23 may be used to record and process input from a lid sensor 30, occupancy sensor 32, or any other sensor and to communicate the input to one or more external access client devices such as cell phones, smart phones 300A, computers 300B, such as tablet computers, laptop computers, wearable computers, and the like. In some embodiments, a processing unit 21 and communications array 23 may communicate the input directly to external access client 300A, 300B, devices through Bluetooth, Wifi, NFC, or other wireless communications, thereby triggering a notification such as a text message, email message, push notification, application notification, and the like on an external access client device. In other embodiments, a processing unit 21 and communications array 23 may communicate the input over a network to external access client devices 300A, 300B, through Wifi, cellular communications, or other wireless communications, thereby triggering a notification such as a text message, email message, push notification, application notification, and the like on an external access client device 300A, 300B. In further embodiments, a processing unit 21 and communications array 23 may communicate the input directly to external access client devices 300A, 300B, and/or communicate the input over a network to external access client devices 300A, 300B, through Wifi, cellular communications, or other wireless communications, thereby triggering a notification such as a text message, email message, push notification, application notification, and the like on an external access client device 300A, 300B. In still further embodiments, a processing unit 21 and communications array 23 may be in wired communication with an external access client devices 300A, 300B, and the processing unit 21 may communicate the input directly to external access client devices 300A, 300B, thereby triggering a notification such as a text message, email message, push notification, application notification, and the like on an external access client device 300A, 300B.

In some embodiments, the communications array 23 may be in wireless communication with an external access client device 300A, 300B, and when the wireless communication is broken, the processing unit 21 may trigger an audio, visual, and/or tactile alert. For example, the communications array 23 may be in Bluetooth wireless communication with the smart phone device 300A of a user. If the user, with their smart phone device 300A, forgets and leaves the case 100 behind, the wireless communication may be broken as the distance between the case 100 and the smart phone device 300A becomes too great for Bluetooth communication. Once the, wireless communication is broken, the processing unit 21 may trigger an alert, such as a sound from the sound device 35, a vibration from a vibration device 38, or a light from the light emitting device 39. In still further embodiments, as the distance between the case 100 and the smart phone device 300A approaches a distance too great for Bluetooth communication, the communication array may send a wireless communication to the smart phone device 300A and the smart phone device 300A may produce an alert.

The processing unit 21 may comprise a clock or timer program 28 (FIG. 9) which may record the time of a sensor event, the time between sensor events, or any other temporal parameter. The processing unit 21 may be configured to operate the communications array 23, sound device 35, a vibration device 38, and/or a light emitting device 39 based on the temporal data provided by the clock or timer program 28 and based on sensor data received or not received allowing the case to audibly, visually, vibrationally, and/or wirelessly communicate the temporal and/or sensor data.

In some embodiments, the microcontroller 21 may operate the communications array 23, light emitting device 39, sound device 35, and/or a vibration device 38 after receiving or not receiving input from a lid sensor 30. For example, the processing unit 21 may or may not receive input from a lid sensor 30 for a period of time or at a certain time such as a user bed time. If the lid sensor 30 does not detect that the lid has been opened or otherwise operated, the processing unit 21 may operate the communications array 23 to send a wireless electronic communication to an external access client device 300A, 300B, such as with a Bluetooth or WiFi wireless communication to notify a user that the lid 11 has not been opened for a period of time or at a certain time. In further embodiments, a processing unit 21 may receive input from a lid sensor 30 or any other sensor detecting if and when an intraoral device is in the cavity 13 or if and when the lid 11 has been opened, and the processing unit 21 may operate the sound device 35 to produce an audible sound, and/or operate the vibration device 38 to produce vibrations to notify a user of the sensor input, and/or a light emitting device 39 to emit light for a visual alert.

In some embodiments, the microcontroller 21 may operate the communications array 23, sound device 35, light emitting device 39, and/or a vibration device 38 after receiving or not receiving input from an occupancy sensor 32. For example, the processing unit 21 may receive input from an occupancy sensor 32 that an intraoral device 200 is detected, such as by being in the cavity 13, for a period of time. Once the period of time meets or exceeds a threshold, such as meeting or exceeding the period of time for a user to eat a meal, the processing unit 21 may operate a communications array 23. After an intraoral device 200 is detected, such as by being in the cavity 13, for a period of time, the processing unit 21 may operate the communications array 23 to send a wireless electronic communication to an external access client device 300A, 300B, such as with a Bluetooth or WiFi wireless communication to notify a user of the sensor input. Likewise, after the intraoral device 200 is detected, such as by being in the cavity 13, for a period of time, the processing unit 21 may operate the sound device 35 to produce an audible sound, and/or operate the vibration device 38 to produce vibrations to notify a user of the sensor input, and/or operate the light emitting device 39 to produce a visual alert. In another example, the processing unit 21 may receive input from an occupancy sensor 32 that an intraoral device 200 is detected, such as by being in the cavity 13, for a period of time such as a sleep period when the user should be wearing the intraoral device. If the intraoral device 200 is detected, such as by being in the cavity 13, during the sleep time period, such as between 10 PM and 6 AM, the processing unit 21 may operate the communications array 23, sound device 35, a vibration device 38, and/or a light emitting device 39, when the intraoral device 200 is detected, such as by being in the cavity 13, during the 10 PM and 6 AM time period.

In some embodiments, the microcontroller 21 may operate the sound device 35, light emitting device 39, and/or a vibration device 38 after receiving or not receiving input from the communications array 23. For example, an external access client device 300A, 300B, may be in wireless communication with the communications array 23 of the case 100. Upon receiving a certain wireless communication or command from the client device 300A, 300B, the processing unit 21 may operate the sound device 35 to produce an audible alert sound, a light emitting device 39 to emit light for a visual alert, and/or operate the vibration device 38 to produce alert vibrations to notify a user of the location of the case 100. In another example, if the wireless communication with the communications array 23 does not receive a wireless communication from an external access client device 300A, 300B, such as within a certain period of time, the processing unit 21 may operate the sound device 35 to produce an audible alert sound, a light emitting device 39 to emit light for a visual alert, and/or operate the vibration device 38 to produce alert vibrations to notify a user of the location of the case 100.

In other preferred embodiments, a processing unit 21 may receive input from a wireless communications array 26, an occupancy sensor 32, lid sensor 30, and/or any other sensor detecting if an intraoral device 200 is in the case 100 and may notify a user by sending a push notification such as a text message, email message, and the like to a client device 300A, 300B. In still further embodiments, a processing unit 21 may receive input from an occupancy sensor 32, lid sensor 30, or any other sensor detecting how much time and at what times an intraoral device 200 is in or out of a case 100. In even further embodiments, a processing unit 21 and communications array 23 may communicate the location of the case 100 and/or give the proximity of the case 100 to a client device 300A, 300B.

While some materials have been provided, in other embodiments, the elements that comprise the case 100 such as the lid 11, base 12, electronic components 19, 20, 21, 22, 23, 25, optional hinge 14, optional lid release 15, optional pressure catch 16, and/or optional floor 18 may be made from durable materials such as aluminum, steel, other metals and metal alloys, wood, hard rubbers, hard plastics, fiber reinforced plastics, carbon fiber, fiber glass, resins, polymers or any other suitable materials including combinations of materials. Additionally, one or more elements may be made from or comprise durable and slightly flexible materials such as soft plastics, silicone, soft rubbers, or any other suitable materials including combinations of materials. In some embodiments, one or more of the elements that comprise the case 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the case 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, slide-to-lock type connection method or any other suitable temporary connection method as one reasonably skilled in the art could envision to serve the same function. In further embodiments, one or more of the elements that comprise the case 100 may be coupled by being one of connected to and integrally formed with another element of the case 100.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An intraoral device holder, comprising:
    a cavity structured to at least partially receive an intraoral device; and
    an occupancy sensor comprising an emitter and a receiver, the occupancy sensor configured to detect the presence of the intraoral device at least partially located within the cavity, and to detect the absence of at least a portion of the intraoral device from the cavity.

2. The intraoral device holder of claim 1, further comprising a timer configured to time an amount of time at least a portion of the intraoral device is detected to be present in and/or absent from the cavity.

3. The intraoral device holder of claim 2, further comprising an alert device configured to provide an auditory, tactile, or visual alert based on the amount of time at least a portion of the intraoral device is detected to be present in and/or absent from the cavity.

4. The intraoral device holder of claim 1, further comprising:
    an alert device configured to provide an auditory, tactile, or visual alert; and
    a communication array configured to communicate with an external device.

5. The intraoral device holder of claim 4, wherein the alert device is configured to provide the alert after a direct or indirect signal from the external device is received by the communication array.

6. The intraoral device holder of claim 1, further comprising a communication array configured to transmit data to an external device, the data comprising instructions for an external device to provide an auditory, tactile, and/or visual alert.

7. The intraoral device holder of claim 6, wherein the communication array is configured to transmit the data when:
    the occupancy sensor detects the presence of the intraoral device at least partially located within the cavity; and
    a strength of a signal from the external device received by the communication array is below a threshold.

8. An intraoral device holder, comprising:
    a cavity configured to at least partially receive an intraoral device;
    an occupancy sensor comprising an emitter and a receiver, the occupancy sensor configured to detect whether the intraoral device is at least partially located within the cavity; and
    a communication array configured to transmit data corresponding to one or more feature of the intraoral device, the one or more feature having been detected while the intraoral device was located within the cavity.

9. The intraoral device holder of claim 8, wherein the transmitted data comprises data corresponding to a feature of a time the intraoral device was in the cavity.

10. The intraoral device holder of claim 8, wherein the communication array is configured to transmit the data while the intraoral device is detected within the cavity.

11. The intraoral device holder of claim 8, wherein the communication array is configured to transmit the data after the intraoral device is detected within the cavity for a period of time.

12. The intraoral device holder of claim 11, wherein the period of time is based on a continuous period of time.

13. The intraoral device holder of claim 11, wherein the period of time is based on a cumulative period of time.

14. The intraoral device holder of claim 8, wherein the communication array is configured to transmit the data while the intraoral device is not detected within the cavity.

15. The intraoral device holder of claim 14, wherein the communication array is further configured to transmit the data at a specific time of day.

16. The intraoral device holder of claim 8, wherein the transmitted data comprises data corresponding to a feature of an amount of the intraoral device received by the cavity.

17. An intraoral device storage device, comprising:
    a cavity structured to at least partially receive an intraoral device, the cavity having a floor; and
    an occupancy sensor at least partially located above the floor, wherein the cavity is structured such that at least a portion of the intraoral device may directly contact an upper surface of the floor when the intraoral device is at least partially received by the cavity.

18. The intraoral device storage device of claim 17, wherein the occupancy sensor is electrically connected to an electronic component located below the floor.

19. The intraoral device storage device of claim 17, wherein the occupancy sensor is positioned to sense the intraoral device in a direction substantially parallel to a major plane of the floor.

20. The intraoral device storage device of claim 17, wherein the occupancy sensor is structured to maintain a relative position to the floor, regardless of whether the intraoral device is at least partially located in the cavity.

* * * * *